US010413257B2

United States Patent
Metzler et al.

(10) Patent No.: US 10,413,257 B2
(45) Date of Patent: Sep. 17, 2019

(54) APPARATUS AND METHOD FOR COLLECTING SUPER-SAMPLED IMAGING DATA

(71) Applicant: The Trustees of The University of Pennsylvania, Philadelphia, PA (US)

(72) Inventors: Scott Dean Metzler, Haddonfield, NJ (US); Samuel Matej, Springfield, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 610 days.

(21) Appl. No.: 14/769,622

(22) PCT Filed: Mar. 6, 2014

(86) PCT No.: PCT/US2014/021256
§ 371 (c)(1),
(2) Date: Aug. 21, 2015

(87) PCT Pub. No.: WO2014/138418
PCT Pub. Date: Sep. 12, 2014

(65) Prior Publication Data
US 2016/0000388 A1    Jan. 7, 2016

Related U.S. Application Data

(60) Provisional application No. 61/773,654, filed on Mar. 6, 2013.

(51) Int. Cl.
*A61B 6/04* (2006.01)
*A61B 6/03* (2006.01)
(Continued)

(52) U.S. Cl.
CPC ............ *A61B 6/0457* (2013.01); *A61B 6/037* (2013.01); *A61B 6/0407* (2013.01);
(Continued)

(58) Field of Classification Search
CPC ...... A61B 6/0407; A61B 6/0457; A61B 6/037
See application file for complete search history.

(56) References Cited

U.S. PATENT DOCUMENTS

| 5,448,607 A | 9/1995 | McKenna |
| 5,777,331 A | 7/1998 | Muehllehner |

(Continued)

OTHER PUBLICATIONS

Li et al. "Image reconstructions from super-sampled data sets with resolution modeling in PET imaging." Med Phys 41(12) (Dec. 2014), 14 pages.*

(Continued)

*Primary Examiner* — Angela M Hoffa
(74) *Attorney, Agent, or Firm* — BakerHostetler (57) ABSTRACT

An apparatus for collecting super-sampled imaging data includes an imaging scanner, a bed, and a first motor. The imaging scanner includes a plurality of detectors arranged substantially circumferentially about a scanner axis. The bed has a plane and a central axis that is generally in the plane of the bed. However, the bed is oriented so as to form a first non-zero degree angle between the central axis and the scanner axis. The first motor translates the bed along the central axis, and a second motor may translate the bed along an axis orthogonal to the central axis and scanner axis. Since the voxels pass through the scanner in different relative positions of the bed, additional information may be acquired during the scan.

21 Claims, 10 Drawing Sheets

(51) Int. Cl.
  *A61B 6/00* (2006.01)
  *G01T 1/161* (2006.01)
  *G01T 1/29* (2006.01)

(52) U.S. Cl.
  CPC .......... *A61B 6/4258* (2013.01); *A61B 6/4275* (2013.01); *A61B 6/5205* (2013.01); *A61B 6/54* (2013.01); *G01T 1/161* (2013.01); *G01T 1/2964* (2013.01); *G01T 1/2985* (2013.01)

(56) References Cited

U.S. PATENT DOCUMENTS

| | | | | |
|---|---|---|---|---|
| 5,966,422 | A * | 10/1999 | Dafni | A61B 6/032 378/15 |
| 6,118,839 | A * | 9/2000 | Dafni | A61B 6/032 378/15 |
| 6,885,165 | B2 | 4/2005 | Henley et al. | |
| 6,915,004 | B2 * | 7/2005 | Newport | G06T 11/005 128/922 |
| 7,038,212 | B2 * | 5/2006 | Wollenweber | G01T 1/2985 250/363.03 |
| 7,640,607 | B2 * | 1/2010 | Guertin | A61B 6/032 378/209 |
| 7,750,304 | B2 * | 7/2010 | Wang | G06T 11/005 250/361 R |
| 7,970,214 | B2 * | 6/2011 | Kadrmas | G06T 11/003 382/232 |
| 7,983,380 | B2 * | 7/2011 | Guertin | A61B 5/064 378/4 |
| 8,218,841 | B2 * | 7/2012 | Kadrmas | G06T 11/003 382/128 |
| 8,466,419 | B2 * | 6/2013 | Gagnon | G01T 1/2985 250/363.06 |
| 9,498,167 | B2 * | 11/2016 | Mostafavi | A61B 5/064 |
| 9,645,261 | B2 * | 5/2017 | Panin | G01T 1/2985 |
| 2003/0161521 | A1 * | 8/2003 | Newport | G06T 11/005 382/131 |
| 2005/0242288 | A1 * | 11/2005 | Wollenweber | G01T 1/2985 250/369 |
| 2007/0003010 | A1 * | 1/2007 | Guertin | A61B 6/032 378/63 |
| 2007/0003021 | A1 * | 1/2007 | Guertin | A61B 6/032 378/208 |
| 2007/0014391 | A1 * | 1/2007 | Mostafavi | A61B 6/032 378/63 |
| 2007/0085012 | A1 | 4/2007 | Thompson | |
| 2008/0180580 | A1 * | 7/2008 | Kadrmas | G06T 11/003 348/744 |
| 2008/0273659 | A1 * | 11/2008 | Guertin | A61B 6/032 378/65 |
| 2008/0287801 | A1 | 11/2008 | Magnin et al. | |
| 2009/0238337 | A1 * | 9/2009 | Wang | G06T 11/005 378/62 |
| 2011/0079722 | A1 * | 4/2011 | Gagnon | G01T 1/2985 250/362 |
| 2011/0216963 | A1 * | 9/2011 | Kadrmas | G06T 11/003 382/154 |
| 2011/0313231 | A1 * | 12/2011 | Guertin | A61B 6/032 600/1 |
| 2014/0200848 | A1 * | 7/2014 | Panin | G01T 1/2985 702/179 |
| 2014/0364718 | A1 * | 12/2014 | Teshigawara | A61B 6/0407 600/407 |
| 2016/0303401 | A1 * | 10/2016 | Mostafavi | A61B 6/032 |
| 2017/0258414 | A1 * | 9/2017 | Guertin | A61B 6/032 |

OTHER PUBLICATIONS

Metzler et al. "Super-Resolution PET using Stepping of a Deliberately Misaligned Bed." 12th Intl Meeting on Fully 3D Image Reconstruction in Radiol and Nucl Medi (Lake Tahoe, CA, Jun. 3013), pp. 388-391.*

* cited by examiner

Fig. 10

APPARATUS AND METHOD FOR COLLECTING SUPER-SAMPLED IMAGING DATA

CROSS-REFERENCE TO RELATED APPLICATIONS

This application is the National Stage of International Application No. PCT/US2014/021256 filed Mar. 6, 2014, which claims the benefit of and priority to U.S. Provisional Application No. 61/773,654, filed Mar. 6, 2013, the entireties of which applications are incorporated herein by reference for any and all purposes.

TECHNICAL FIELD

The present invention relates generally to radiological imaging and more specifically relates to super-sampling of radiological data.

BACKGROUND

There were an estimated 2.5 million PET scans in the U.S. alone in 2012. There were an estimated 900,000 PET scans in Western Europe in 2011. Worldwide, there continues to be rapid growth of PET scans. Therefore, improvements in PET-reconstruction quality have a very high impact on patient care.

Super-resolution is a well-established technique, often used in image processing. This technique requires super-sampled data as input. It has been demonstrated that super-sampling, such as "wobbling" the scanner by a few millimeters, can substantially improve image quality and reduce artifacts; however, there are practical problems with implementing wobbling for whole-body scanners. For example, wobbling the scanner requires additional hardware for moving the scanner or patient. Moreover, current PET scanners no longer do this for a combination of reasons: (1) it was believed that super-sampling no longer added any useful information after technological breakthroughs allowed the pixel size of the detectors to be reduced; (2) manufacturers dropped wobbling because it is mechanically cumbersome; and (3) it added cost to have this additional hardware for wobbling the scanner.

Figure 1:
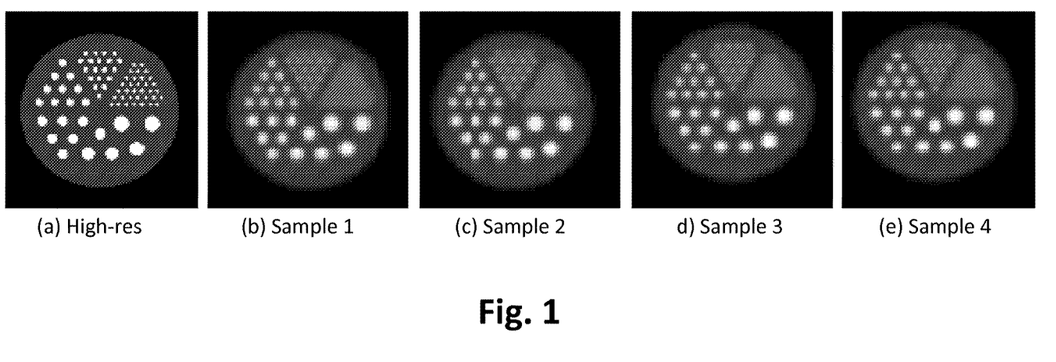
Figure 2:
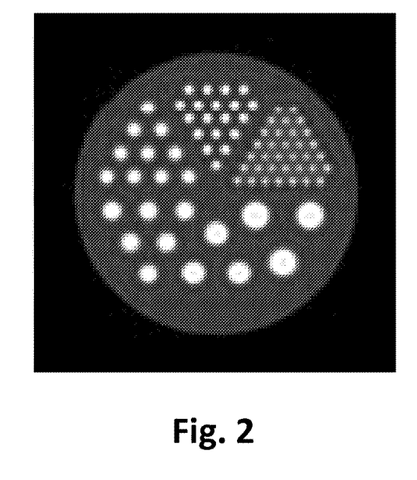
FIG. 2 is an example image illustrating super-resolution using post-reconstruction algorithm on images (b)-(e) in FIG. 1.

FIG. 1 and FIG. 2 illustrate current techniques of super-resolution reconstructions and super-sampling. Digital images such as PET reconstructions inherently average over an area or volume to produce pixel/volume values. FIG. 1 illustrates several examples of the effect of that averaging by shifting the edge of the first pixel between down samples ((b)-(e)). Because the pixels in the images represent averages of overlapping but different regions, there is greater information content in the set of images than in any individual image. Super-sampling allows one to recover higher-quality images, depending on the resolution of the imaging system.

FIG. 1 (*a*) is a high resolution image (512×512; 0.125 mm pixels) of a hot-rod phantom (50 mm diameter; rod diameters: 1.2, 1.6, 2.4, 3.2, 4.0, and 4.8 mm) on a warm background (hot:back=5:1). The image is blurred (1.5 mm FWHM Gaussian) and down-sampled to 64×64 (1 mm) pixels in (b)-(e), but with relative shifts in the horizontal and vertical direction (in mm) of (0,0), (−2.5,0), (0,−2.5), and (−2.5,−2.5), respectively. This half-integer bin shifting (2.5 instead of 2) results in averaging different high-res pixels in (a) into lower resolution pixels for (b)-(e).

FIG. 2 illustrates the result of super-resolution using a post-reconstruction algorithm to combine the four samples in FIG. 1 ((b)-(e)), each on a 64×64 grid, back into a 512×512 grid (as in the high-resolution image in FIG. 1(*a*)). The original resolution is not fully restored (due to Gaussian blur, which is not yet modeled in the algorithm, and information loss from down sampling), but the image's improved resolution signifies information recovery.

A method is desired that allows for the acquisition of super-sampled data at very low cost, without use of a post-reconstruction algorithm as in the example of FIGS. 1 and 2 or additional hardware in the scanner. The present invention addresses these needs in the art.

SUMMARY

An apparatus is provided for collecting super-sampled imaging data. The apparatus for collecting super-sampled imaging data includes an imaging scanner, a bed, and a first motor. The imaging scanner may include a plurality of detectors arranged substantially circumferentially about a scanner axis. The bed has a plane and a central axis that is generally in the plane of the bed. The bed also has an orientation that forms a first non-zero degree angle between the central axis and the scanner axis. The first motor translates the bed along the central axis.

Methods for collecting super-sampled imaging data using such an apparatus are also disclosed. For example, a subject that has been treated with a radioactive tracer capable of emitting or causing the emission of a detectable particle or ray, is positioned on a bed that has a plane and a central axis that is generally in the plane of the bed. The bed has an orientation that forms a first non-zero degree angle between the central axis and the scanner axis. The bed may be translated along the central axis and a detectable particle or ray is detected with a scanner including a plurality of detectors arranged substantially circumferentially about the scanner axis. The steps of translating the bed along the central axis and detecting the detectable particle with the scanner may be repeated to super-sample the image data.

BRIEF DESCRIPTION OF THE DRAWINGS

The present application is further understood when read in conjunction with the appended drawings. For the purpose of illustrating the claimed subject matter, there are shown in the drawings exemplary embodiments of the claimed subject matter; however, the presently disclosed subject matter is not limited to the specific methods, devices, and systems disclosed. In addition, the drawings are not necessarily drawn to scale. In the drawings:

FIGS. 1(*a*)-1(*e*) are example images illustrating the effect of averaging by half-integer bin shifting the edge of the first pixel in reconstructions;

DETAILED DESCRIPTION OF ILLUSTRATIVE EMBODIMENTS

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the features and methods of making and using apparatuses for collection of a super-sample of data, as well as the apparatuses themselves, and vice versa.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Overview

Embodiments described herein provide methods and apparatuses for acquiring super-resolution data in Positron Emission Tomography (PET) and may also be applicable to Single Photon Emission Computed Tomography (SPECT) and Computed Tomography (CT). For example, super-resolution data may be obtained by super-sampling voxels during acquisition through near-continuous motion of a patient bed along a direction intentionally—but carefully and accurately—misaligned with respect to the scanner's axial direction. By acquiring super-resolution data, substantial improvement in reconstruction accuracy may be obtained for imaging systems including a PET, SPECT, or CT whole body system.

In an example embodiment, a small angle is introduced in the patient bed's motion in the horizontal and/or vertical direction relative to the axial direction of the scanner (e.g., PET scanner). This may allow the Lines of Response (LORs) of the PET scanner to pass through volume elements (voxels) differently as the patient passes through the scanner. Since the voxels pass through the scanner in different relative positions, additional information may be acquired during the scan. This additional information may be used in reconstruction to both improve resolution and reduce artifacts.

Embodiments described herein may be used to acquire super-sampled data in PET scanners, which may allow better reconstructions without introducing a mechanical method for wobbling their heavy scanners. The techniques described herein may also be applied to other tomography devices, such as SPECT and CT. Moreover, the embodiments may be used as an inexpensive retrofit to installed scanners for improving their resolution and extending their useful service lifetimes. The retrofit may involve introducing a careful rotation of the bed, which may be easy, and an upgrade to reconstruction and acquisition software. The embodiments may also be applicable to small-animal versions of PET, SPECT, and CT scanners.

Two important characteristics of scanners have changed since their commercial introduction, making it important to reconsider super-sampling for obtaining super-sampled data for existing and future scanners: (i) scanners are now 3D, providing more counts, which allows accurate reconstruction of higher-resolution structures; and (ii) iterative algorithms with resolution modeling have changed again the relationship between sampling and resolution, making it important to increase the number of samples. Super-sampling may allow resolution improvement with iterative algorithms using resolution-recovery techniques, beyond what those algorithms can achieve without super-sampling.

Clinical acquisitions often use multiple bed positions, where the patient is scanned for a few minutes and then shifted by a fraction of the axial field of view (FOV) along the scanner's axial direction. After the axial shift, the voxels remaining in the FOV have the same position relative to the lines of responses (LORs), at least in the transverse directions (i.e., the horizontal and vertical shifts are zero) and usually in the axial direction. This may be exploited by introducing a small angle between the bed motion and the scanner's axial direction to super-sample in the horizontal direction. In conjunction, the bed may be moved vertically to super-sample in the vertical direction. Axial super-sampling may come from axial bed shifts by a non-integral number of crystal pitches. A side benefit of using nearly continuous axial motion may be axial uniformity of sensitivity (noise).

In general, legacy and current clinical systems do not have 3D position systems; they have in/out and up/down positioning, but not side-to-side. The embodiments described herein couples the in/out and horizontal directions for 3D super-sampling using existing motors. Moreover, the embodiments may be applicable to small-animal systems.

The embodiments described herein enables super-sampling in clinical imaging, such as PET, without additional hardware, removing an important obstacle for vendors. Instead of carefully aligning beds with the axial direction, beds may be carefully aligned in a slightly different direction. Otherwise, the changes may be only in acquisition and reconstruction software, especially since many acquisitions are already performed in list-mode (i.e., the data size may not be increased by the method of the invention).

In an example embodiment, by super-sampling, which increases the effective number of LORs, the reconstruction may use a larger number of finer voxels without aliasing artifacts. Thus, it may be possible to improve resolution for the same scanner without changing the hardware, especially by providing more data for resolution-recovery algorithms.

Embodiments described herein also may be applied as a retrofit to existing scanners because the changes needed are to the bed alignment and the acquisition and reconstruction software. This may provide a practical and inexpensive upgrade path for existing installations.

In accordance with an example embodiment, the PET-acquisition procedure may be generalized to measure super-sampled lines of response (LORs) when the bed moves through the scanner instead of redundantly measuring the same lines (e.g., axial shift without horizontal or vertical shifts). Nearly continuous motion may be utilized. Embodiments described herein may also utilize axial super-sampling, making the super-sampling 3D.

Throughout this disclosure reference is often made to photon emission tomography (PET). Use of the phrase PET is exemplary and non-limiting and a person of ordinary skill in the art will appreciate the applicability of the methods and apparatuses of the invention to other forms of radiological imaging, including single photon emission computed tomography (SPECT) and computed tomography (CT).

Exemplary Embodiments

Figure 3:
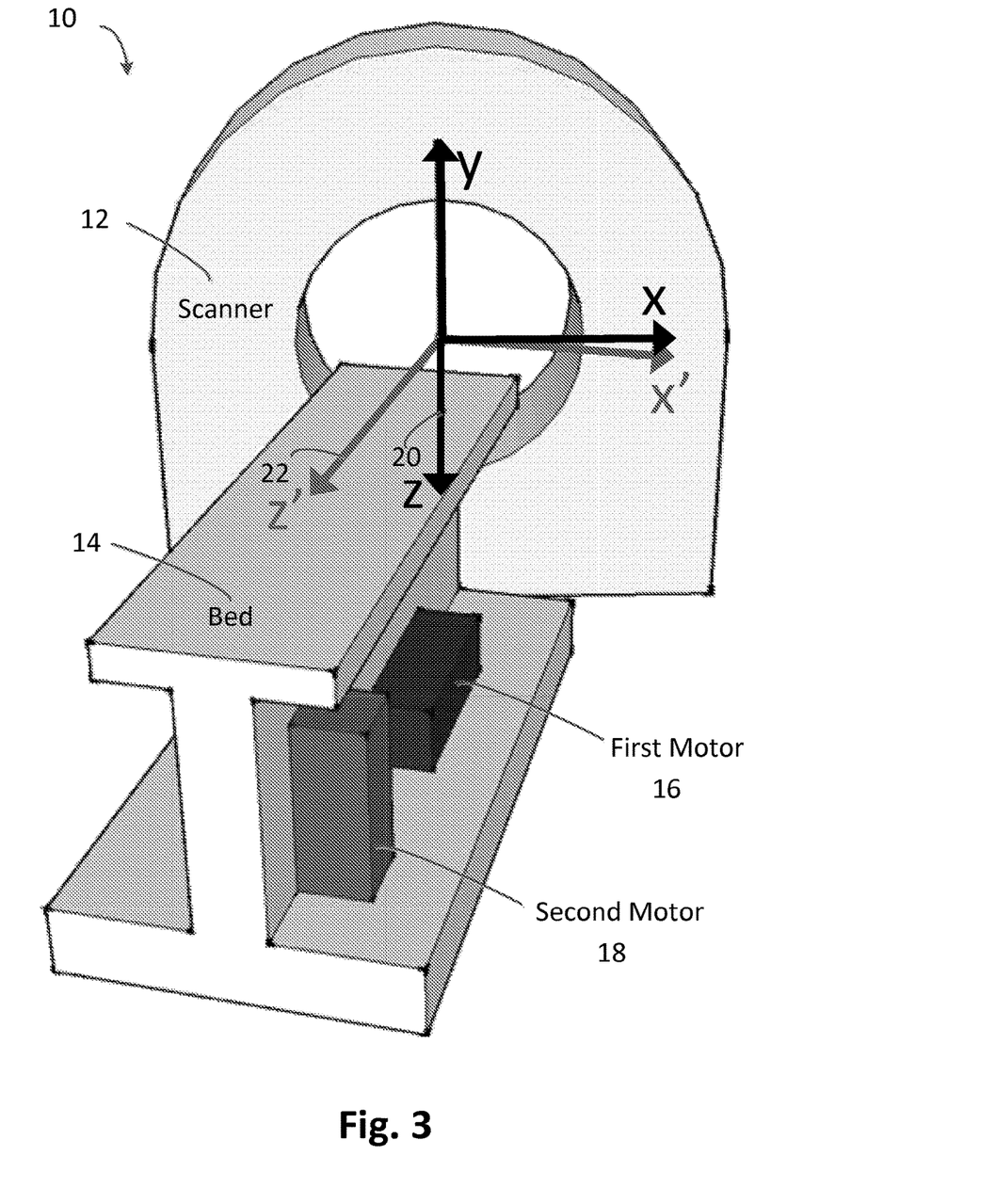
FIG. 3 is a diagram illustrating an apparatus for collecting super-sampled imaging data in accordance with an example embodiment.

FIG. 3 illustrates an apparatus for collecting super-sampled imaging data in accordance with an example embodiment. An apparatus 10 may include an imaging scanner 12, a bed 14 and a first motor 16. The imaging scanner 12 may include one or more, such as a plurality, of detectors arranged substantially circumferentially about a scanner axis. As used herein the terms "scanner axis" 20 and "z-axis" 20 are used interchangeably. In an example embodiment, the scanner 12 may include a plurality of x-ray tubes or other radiation transmitters arranged together with one or more radiation detectors substantially circumferentially about the scanner axis 20. Example scanner arrangements may be in traditional PET, SPECT, or CT scanners. For example, the scanner 12 may have one or more radiation transmitters (such as x-ray tubes) opposed from a detector arc (or flat panel). In another example embodiment, the scanner 12 may have more than one radiation transmitter (such as x-ray tubes) having a corresponding number of detectors arranged so that they minimally interfere with each other (e.g., Tube 1 at 0 deg, Tube 2 at 90 deg., Det. 1 at 180 deg., Det 2 at 270 deg.).

The bed 14 may have a plane and a central axis 22 that is generally in the plane of the bed 14. For example, the plane of the bed 14 may be used for positioning a subject such as a patient or an object to be imaged using the apparatus 10. The plane of the bed 14 may include the scanner axis 20 and the central axis 22. As used herein the terms "central axis" 22 and z'-axis 22 are used interchangeably and also describe a possible direction of the bed motion.

As illustrated in FIG. 3, the bed 14 may have an orientation that forms a first non-zero degree angle between the central axis 22 and the scanner axis 20. The first non-zero degree angle is often referred to as "α" throughout this disclosure. In an example embodiment, the bed 14 may have an orientation that forms a second non-zero degree angle between the central axis 22 and an axis orthogonal to the scanner axis 20. The axis orthogonal to the scanner axis 20 may be a vertical axis, a horizontal axis, or any other axis that is oriented 90° from the scanner axis 20. Depending on the geometry of the apparatus 10 (e.g., the scanner diameter, crystal size, reconstruction parameters, etc.), certain angles can optimize the Sampling Uniformity Metric described herein. That is, depending on the geometry of the apparatus 10, certain angles may maximize the sampling uniformity. In another example embodiment, the first non-zero degree angle is an angle that maximizes sampling uniformity. In other embodiments, the second non-zero degree angle is also an angle that maximizes sampling uniformity.

The first motor 16 may translate the bed 14 along the central axis 22. The first motor 16 may be manual, electronic, or computerized. The apparatus 10 may also include a second motor 18 for translating the bed 14 along an axis orthogonal to the scanner axis 20. The axis orthogonal to the scanner axis 20 may be orthogonal to both the central 22 and scanner axes 20.

In an example embodiment, the apparatus 10 may also include one or more actuators that can change the orientation of the bed 14 and thereby change the first non-zero degree angle. In another example embodiment, an apparatus 10 may include one or more actuators that can change the orientation of the bed 14 and thereby change the second non-zero degree angle. Such actuator can be manual, electronic, or computerized. An example of such an actuator is the foot-anchor described herein.

In some embodiments, one or more of the plurality of detectors are capable of detecting gamma rays, x-rays or a combination of gamma-rays and x-rays. The plurality of detectors may be any detector as commonly used in radiological imaging devices, including radiological imaging such as in PET, CT or SPECT.

Figure 4:
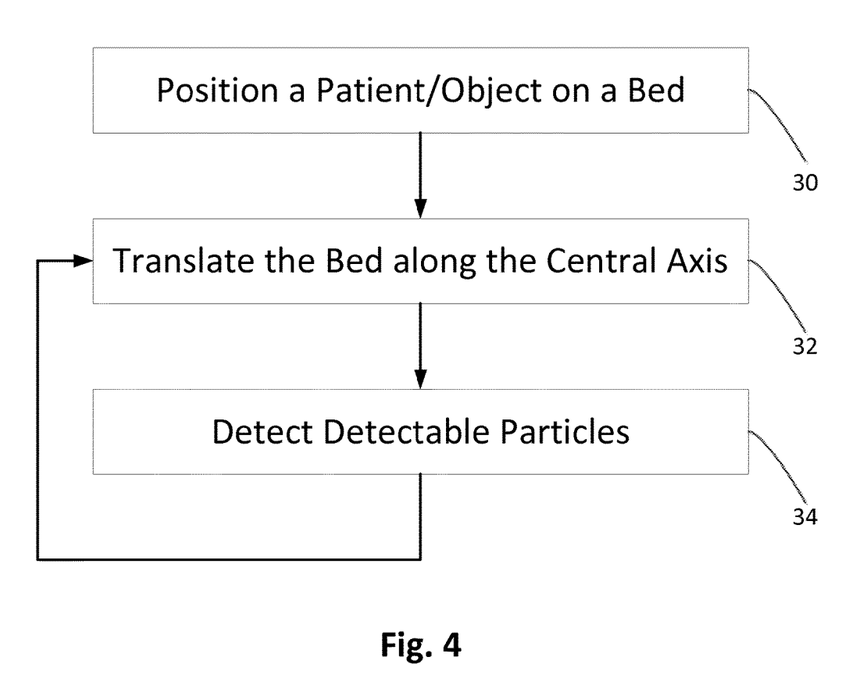
FIG. 4 is a flow diagram illustrating a process for collecting super-sampled imaging data in accordance with an example embodiment.

FIG. 4 illustrates a process for collecting super-sampled imaging data in accordance with an example embodiment. For example, at step 30, a patient or an object that has been treated with a radioactive tracer capable of emitting or causing the emission of a detectable particle or ray, is positioned on a bed that has a plane and a central axis that is generally in the plane. The bed may have an orientation that forms a non-zero degree angle between the central axis and the scanner axis.

The bed may be translated along the central axis at step 32. Translating may refer to changing the spatial position of the bed. In accordance with an example embodiment, translating or moving the bed in the in/out direction can refer to moving the bed along the central axis or the z'-axis. As may be understood from the context, references herein to translating or moving the bed in the in/out direction can refer to moving the bed along the scanner axis or z axis. References herein to translating or moving the bed in the up/down direction can refer to moving the bed along the vertical axis or y-axis, or any axis that is orthogonal to the scanner axis, or in some embodiments, orthogonal to both the central axis and the scanner axis.

In an example embodiment having a first non-zero degree angle between the central axis and the scanner axis and a non-zero degree angle between the central axis and an axis orthogonal to the scanner axis, 3D super-sampled data may be collected by alternately translating the bed in the direction of the central axis and detecting emitted particles and/or rays; that is, 3D super-sampled data may be collected using such an embodiment without translating the bed along an axis orthogonal to the scanner axis. In another example embodiment, 3D super-sampled data may be collected by alternately translating the bed in the direction of the central axis and in the direction of an axis orthogonal to the scanner axis, and detecting emitted particles and/or rays.

The detectable particle or ray may be detected with a scanner at step 34. The scanner may include a plurality of detectors arranged substantially circumferentially about the scanner axis. In an example embodiment, the scanner may include a plurality of x-ray or other transmitters arranged together with a plurality of detectors substantially circumferentially about the scanner axis.

Translating the bed along the central axis at step 32 and detecting detectable particles at step 34 may be repeated. In an example embodiment, the bed may be translated along an axis that is substantially orthogonal to the scanner axis or substantially orthogonal to both the central axis and the scanner axis.

In an example embodiment, the bed may be oriented to form a first non-zero degree angle between the central axis and the scanner axis. The bed may also be angled to change the degree of the first non-zero degree angle. By way of example, the bed may be oriented or angled by using one or more actuators, or the bed may be oriented or angled by using the one or more foot anchors described below.

In another example embodiment, the bed may be oriented to form a second non-zero degree angle between the central axis and an axis that is orthogonal to the scanner axis. The bed may also be angled to change the degree of the second non-zero degree angle. By way of example, the bed may be oriented or angled by using one or more actuators, or the bed may be oriented or angled by using the one or more foot anchors described below.

In an example embodiment, a patient or object may be positioned on a bed that can have a plane and a central axis that is generally in the plane of the bed. The bed may have an orientation that forms a first non-zero degree angle between the central axis and a scanner axis. Radiation may be transmitted from a scanner toward the patient or object, the scanner comprising one or more radiation transmitters and one or more radiation detectors arranged substantially circumferentially about the scanner axis. The bed may be translated along the central axis and the radiation detected with the scanner. The steps of transmitting, translating and detecting may be repeated. In some embodiments, the radiation may be x-ray radiation.

Figure 5:
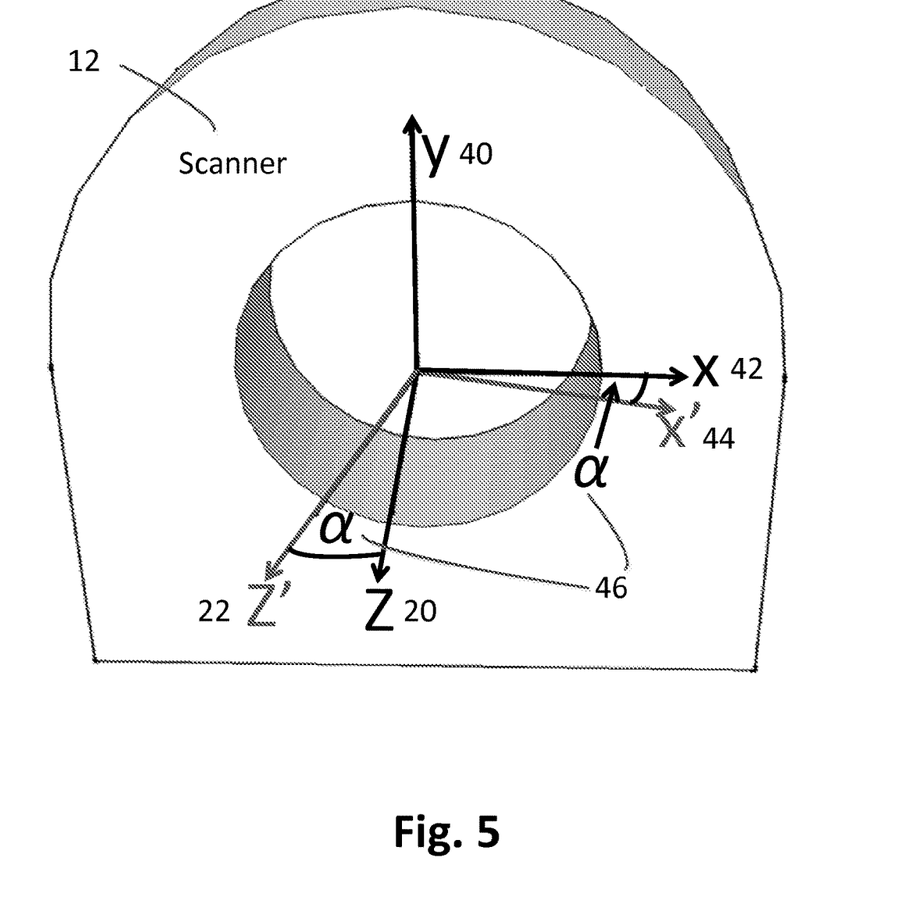
FIG. 5 is a diagram illustrating a right-handed coordinate system to describe PET-scanner geometry in accordance with an example embodiment.

FIG. 5 illustrates a right-handed coordinate system in PTE-scanner geometry in accordance with an example embodiment. The z axis 20 may correspond to the scanner's axial direction. The y axis 40 may be vertical, corresponding to the bed's up/down direction. The x axis 42 may be in the horizontal direction. The z' axis 22 may correspond to the bed's in/out direction. The x' axis 44 may correspond to the side-to-side direction, which typically is not under motorized control. The x' 44 and z' 22 axes may make an angle $\alpha$ 46 with the x 42 and z 20 axes, respectively.

As shown in FIG. 5, the z-axis may be aligned with the scanner's axial direction. The bed's in/out direction (z') may be in an x-z plane, with angle $\alpha$ between its direction and the z axis; the primed axes may be a rotation by $\alpha$ about the y (vertical) direction. The value of $\alpha$ is exaggerated for clarity.

In conventional imaging systems, including conventional PET systems, $\alpha=0$. Consider a point (e.g., a voxel) that does not move relative to the bed. When the bed moves in/out, the voxel's z and z' coordinate values change by the same amount, but the transverse coordinates relative to the scanner (x,y) are unchanged. By introducing a small, non-zero angle for a 46, the voxel's x position relative to the scanner's coordinate system may be changed when the scanner moves in and out. Combining this change in x 42 when z 20 changes with small in/out shifts (i.e., nearly continuous bed motion) and coordinated, small vertical shifts, many samples for a voxel at different shifts relative to the scanner may be obtained.

In an example embodiment, it is unnecessary to lengthen the duration of the scan to acquire the super-sampled acquisition described above. For example, many data sets with relative shifts may be obtained. A small increase in sampling may substantially improve the reconstruction accuracy. In some embodiments, list-mode acquisitions and embedded flags to signal when the bed moved may be used.

In another example embodiment, by introducing a small-angle between the bed motion and the scanner's axial direction, the LORs may pass through the voxels in different locations as the bed moves through the scanner. Bed vertical (y) shifts may improve the sampling in the third dimension. The end result may be more samples during the same total acquisition time.

Figure 6:
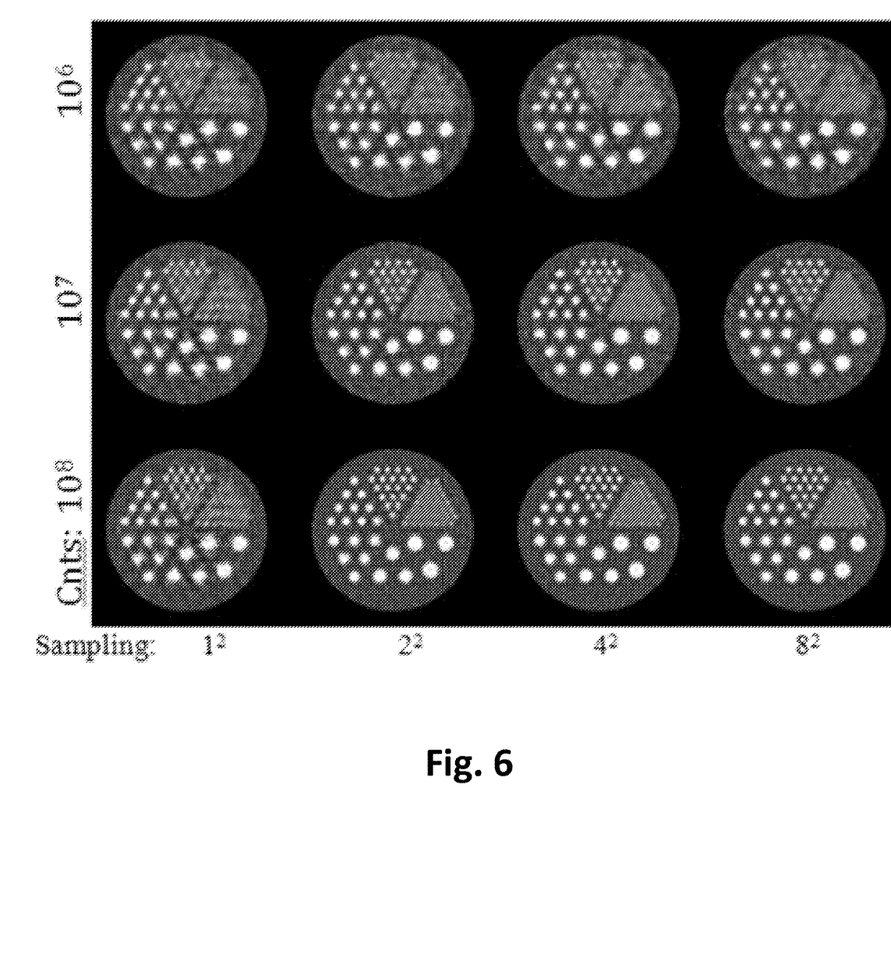
FIG. 6 includes example images illustrating reconstructions from 2D PET acquisitions of a hot-rod phantom in accordance with an example embodiment.

FIG. 6 illustrates reconstructions from 2D PET acquisitions of a hot-rod phantom in a uniform background in accordance with an example embodiment. Different count levels in the acquisitions correspond to the rows. Columns indicate the amount of super-sampling. The first column has only 1 acquisition. Other columns increase the number of sampling positions in each of the 2 dimensions (e.g., $8^2$ sampling is on an 8×8 uniform grid with 64 samples). These reconstructions show the iteration at the minimum normalized error for each case.

In FIG. 6, the rows represent low-, medium-, and high-count ($10^6$, $10^7$, and $10^8$) acquisitions, respectively. The columns are for different 2D sampling configurations. $1^2$ indicates 1 sample, $8^2$ indicates 8 sampling positions in both x and y, 64 total. The rods seen in the smallest sector for the $1^2$ sampling may be artifactual, not occurring in the same position as the phantom.

In an example embodiment, normalized error (NE) may be used as a metric of reconstruction accuracy. This metric is defined for a reconstruction with value $v_1$ in voxel I in comparison to that voxels' true value, $r_i$:

$$d(\vec{r}) = \sum_{x} e^{-\lambda \left[\vec{r} - \vec{r}_x^*\right]^2 / 2}$$

where the overline indicates average values over the voxels and k scales the reconstruction to the reference for fair comparison between iteration number, count level, and sampling techniques. The value of k may be that which minimizes NE: $NE: k = \overline{vr}/\overline{v^2}$.

Figure 7A:
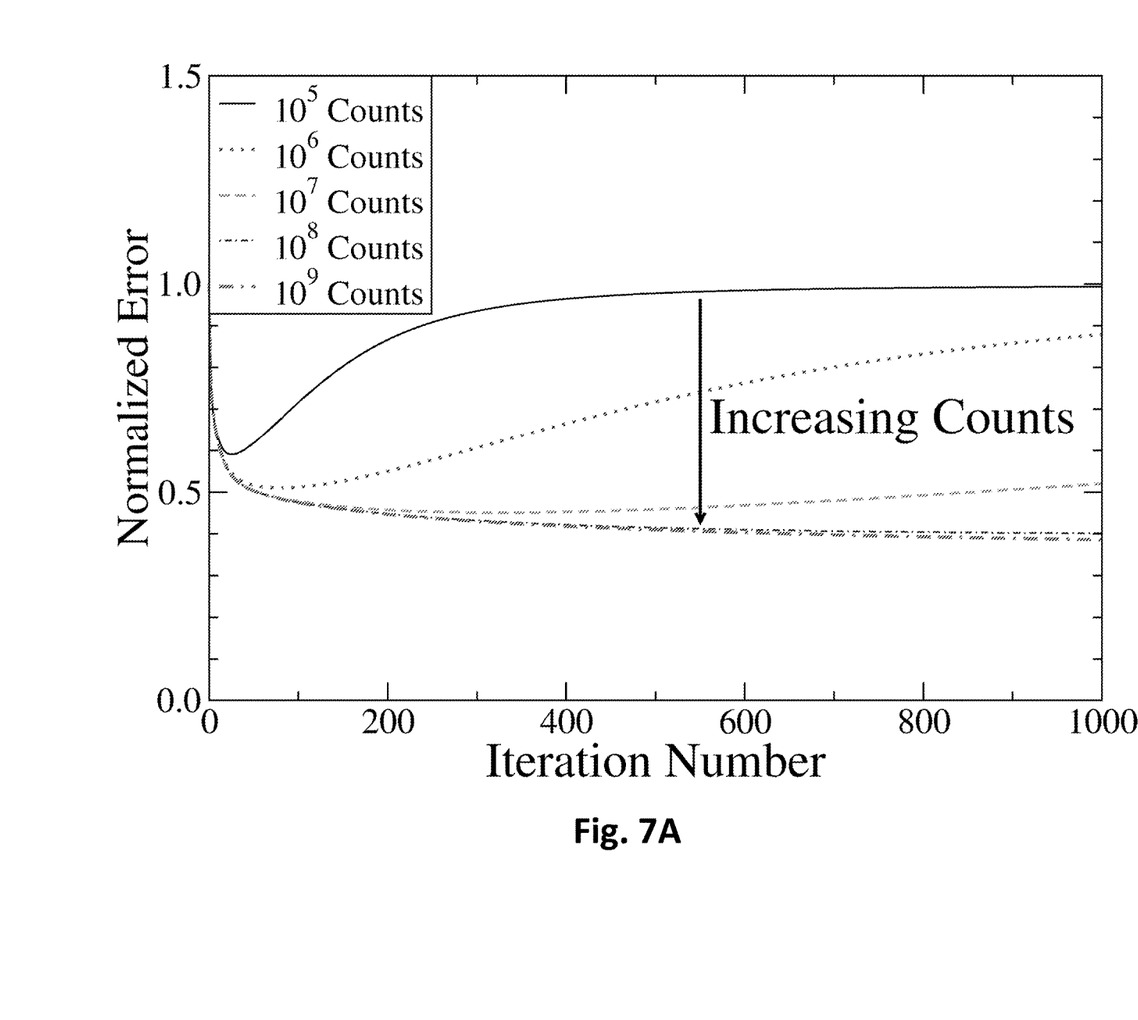
FIG. 7A is a graph illustrating normalized error for the reconstruction as a function of iteration number.
Figure 7B:
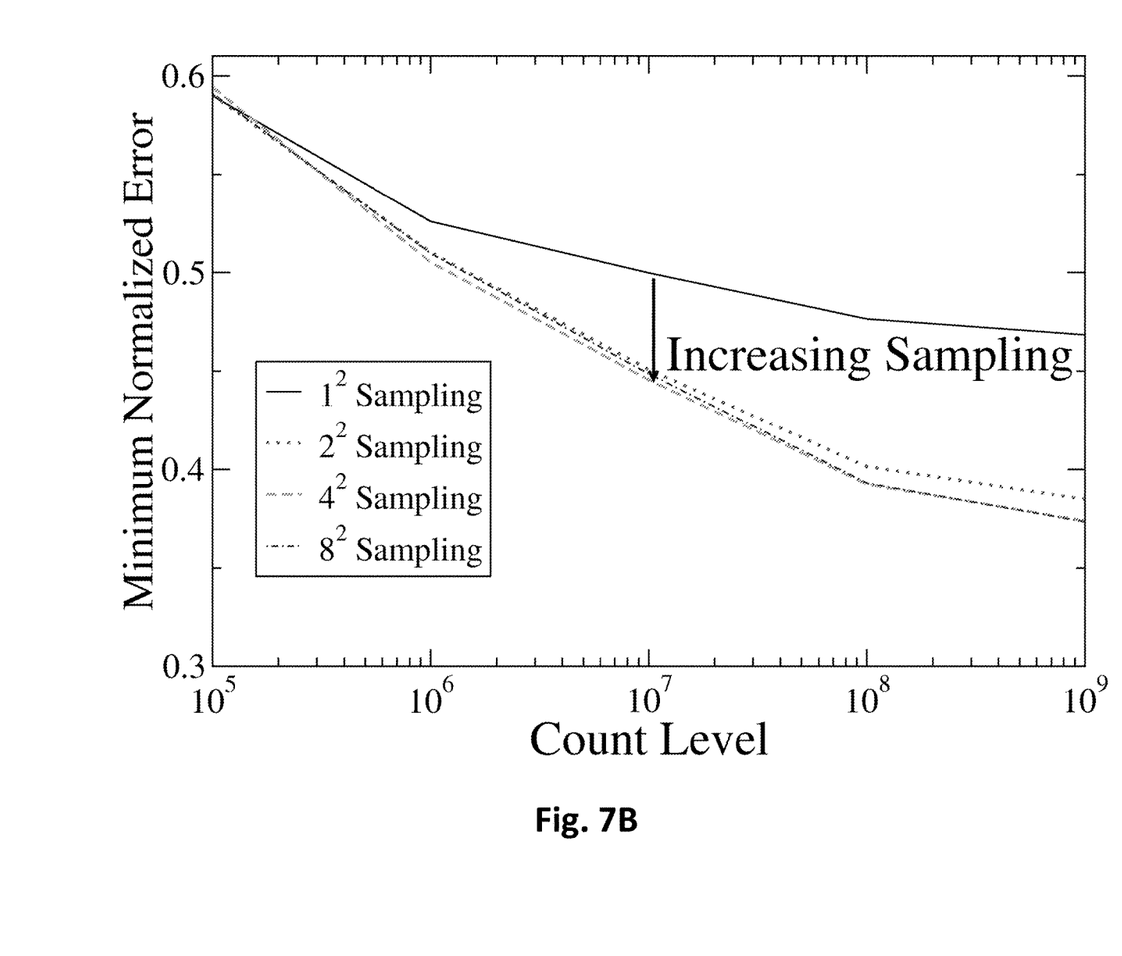
FIG. 7B is a graph illustrating minimum normalized error as a function of count rate for different sampling levels.

FIGS. 7A and 7B illustrate normalized errors for the reconstruction shown in FIG. 6. FIG. 7A shows the $1^2$ sampling for 5 counts levels (only 3 of which are shown in FIG. 6). Each curve shows a minimum. The minimums for the various cases are extracted to show the minimum normalized error NE as a function of count level (per slice) and sampling. In FIG. 7A, this example is for $1^2$ sampling but other samplings show a similar pattern. Each count level shows a minimum for normalized error, but the minimum may occur at different iterations.

FIG. 7B shows that accuracy improves both with count level and increased sampling. More importantly, at all count levels shown (low-count through high-count), there is a clear difference in accuracy between $1^2$ and $2^2$ sampling, but the improvement quickly saturates, showing progressively smaller improvements. This means that even a small improvement in sampling may have large results in the reconstruction accuracy.

In an example embodiment, the uniformity of a voxel's sampling may be evaluated by the normalized standard deviation of the weighted distances of super-sampling points in a unit cell to all points in that cell:

$$NE = \sqrt{\overline{(kv - r^2)}} / \overline{r}$$

where $d(\vec{r})$ is the weighted distance of super-sampling points to integrating point $\vec{r}$ (here $$\sqrt{\overline{d^2} - \overline{d}^2} / \overline{d},$$

with $\lambda=100$ mm$^{-2}$; $\vec{r}_z^*$ is the sampling point's position in the unit cell and the sum is over all sampling points) and $\overline{d^n} = \int d^x(\vec{r})dV/\int dV$ is the average value from the volume integral over the unit cell). Those skilled in the art will appreciate that other sampling metrics may be used to maximize the sampling uniformity.

Figure 8:
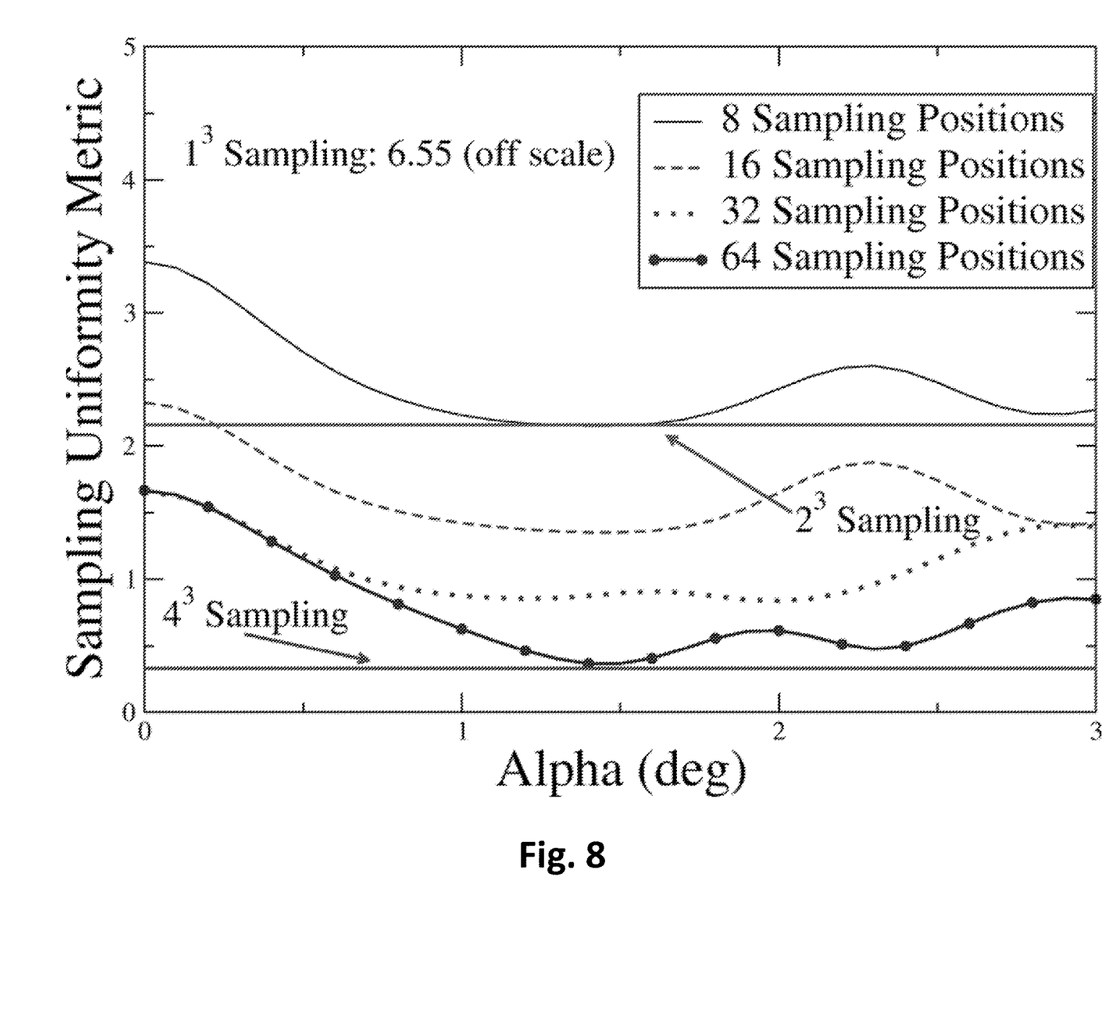
FIG. 8 is a graph illustrating sampling uniformity metrics for sample shift sequences in accordance with an example embodiment.

FIG. 8 illustrates sampling uniformity metrics for sample shift sequences in accordance with an example embodiment. In FIG. 8, reference values are shown for sampling uniformity with this metric for $4^3$ and $2^3$, which is related to the $2^2$ sampling resulting in FIG. 2. This metric may be related to the number of unique samples of a voxel. In FIG. 8, Sampling Uniformity Metric and a for different possible acquisition parameters may represent samples of the full parameter space, while smaller values of this metric may indicate better sampling uniformity. The curves may have more than one minimum, often because of sampling periodicity. A small value for a may lead to a negligible loss in field of view. For comparison, the horizontal lines indicate that the uniformity achieved with a $2^3$ and $4^3$ sampling. In some embodiments, improving the sampling, even by a small amount (e.g., from $1^2$ to $2^2$; doubling in each direction), may have a large effect on reconstruction accuracy, for all count levels (see FIG. 5 and FIG. 7A-B). As illustrated in FIG. 8, there may be configurations that yield uniformity between that of $2^3$ to $4^3$ (i.e., better than $1^3$ to $2^3$).

In an example embodiment, introducing a rotation by the angle α and using vertical shifts, may decrease the effective FOV. For a scanner with bore length L and FOV diameter D, the effective horizontal FOV may be reduced by: L tan α. The effective vertical FOV may be reduced by the range of vertical shifts. FOV reduction can be patient independent.

In another example embodiment, to consider the impact for a realistic configuration (L=19.4 cm; voxel edge: 4 mm; 45 axial voxel slices (N)), a $2^3$-sampling shift sequence (Table 1) may be considered, and the $2^3$-sampling shift sequence may yield substantial reconstruction improvements. Since this can be explicitly listed, using only 8 shifts, it can be a lower bound on sampling improvement. The ratio of x to z shifts can be ε=1/N=1/45; α=1.3°. From this the horizontal FOV may be reduced by 4 mm. Also, the vertical FOV may be reduced by 4 mm or 2 mm. Note: the horizontal and vertical shifts are less than 1 voxel (~4 mm).

Table 1 (below) shows a sequence of 8 acquisitions that double the sampling in each of the 3 dimensions. The Shifts show the bed up/down (y) and the in/out (z) movements between acquisitions and their cumulative effect. The x shift is proportional to the z shift with ratio ε. The cumulative shifts are related back to the unit cell, which has edge length V. N is the number of axial slices.

TABLE 1

| Shift | | Cumulative | | | Unit Cell | | |
|---|---|---|---|---|---|---|---|
| Y | Z | X | Y | Z | X | Y | Z |
| — | — | 0 | 0 | 0 | 0 | 0 | 0 |
| V/2 | 0 | 0 | V/2 | 0 | 0 | V/2 | 0 |
| 0 | V/2 | ε V/2 | V/2 | V/2 | ε V/2 | V/2 | V/2 |
| −V/2 | 0 | ε V/2 | 0 | V/2 | ε V/2 | 0 | V/2 |

TABLE 1-continued

| Shift | | Cumulative | | | Unit Cell | | |
|---|---|---|---|---|---|---|---|
| Y | Z | X | Y | Z | X | Y | Z |
| 0 | (N − 1) V/2 | V/2 | 0 | N V/2 | V/2 | 0 | 0 |
| V/2 | 0 | V/2 | V/2 | N V/2 | V/2 | V/2 | 0 |
| 0 | V/2 | V (1 + ε)/2 | V/2 | (N + 1) V/2 | V (1 + ε)/2 | V/2 | V/2 |

In an example embodiment, the technique of adding a small angle to the bed direction is fully compatible with CT and transmission acquisitions on PET/CT and PET systems, respectively. These may fall into three categories: (i) future PET/CT systems; (ii) legacy PET/CT systems; and (iii) transmission PET systems.

(i) For future PET/CT systems, the most likely implementation may introduce a small rotation between the PET and the CT, leaving the bed aligned with the CT. Thus, there may be no change to the CT and the PET could still be super-sampled. A rigid-body transformation may couple the CT and PET spaces.

(ii) For legacy PET/CT systems, the simplest solution may be to rotate the bed and compensate in the CT software. The PET software may need to be upgraded to correctly handle the super-resolution data. The CT software may be upgraded, if necessary, for a bed-alignment parameter; such calibration parameters may already exist for some CT systems.

(iii) For transmission imaging, the attenuation image, which may be acquired at a small number of the acquisition positions (multiple images may be needed depending on the object's axial length), may need to be translated according to the acquisition sequence in the PET reconstruction; no change to the transmission hardware may be required.

In an example embodiment, existing reconstruction code may be modified to simultaneously reconstruct data from all the acquired positions. The reconstruction may need to account for the position of the patient at the time of acquisition of each imaging datum. Corrections may also need to account for the patient's position at the time of acquisition. Examples may include attenuation, normalization, scatter and/or randoms.

In another example embodiment, the bed alignment may be measured by mounting a point source on the bed and then moving the bed through the scanner during an acquisition. The data may be reconstructed as if the bed were stationary. This may have the effect of transforming the point source into a line source oriented parallel to the bed's direction (z'). The angle α may be easily measured in a coronal slice containing the source.

Figure 9A:
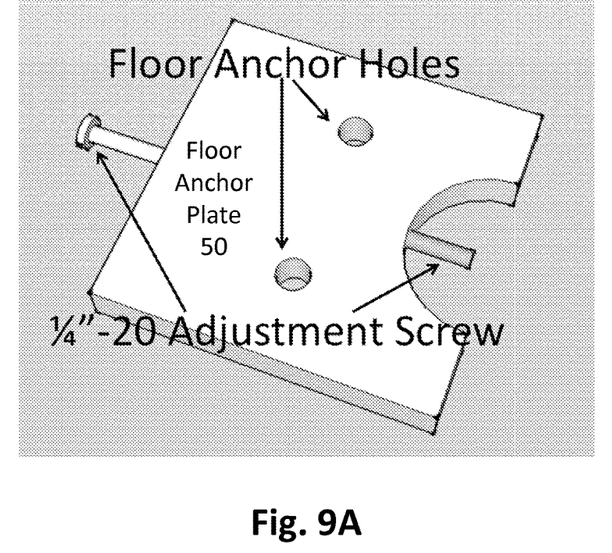
FIG. 9A is a diagram illustrating a floor-anchor plate used to adjust the PET scanner's bed direction in accordance with an example embodiment (the adjustment screw may move the bed ~0.04°/revolution)
Figure 9B:
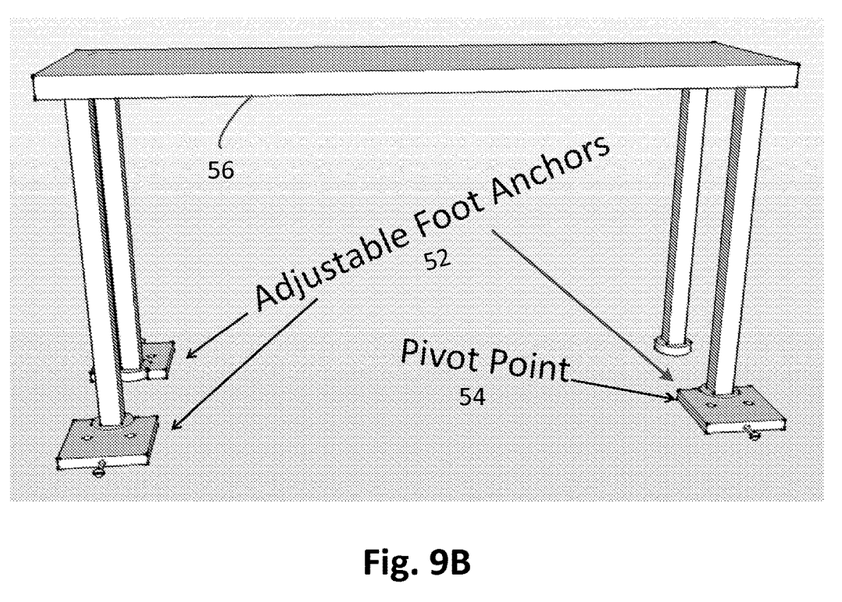
FIG. 9B is a diagram illustrating a bed using three floor anchor plates where one floor anchor may serve as a pivot point and the other two may push the bed in opposing directions in accordance with an example embodiment.

FIG. 9A illustrates a floor-anchor plate 50 used to adjust the bed direction in accordance with an example embodiment. FIG. 9B illustrates a bed 56 using three floor anchor plates 52 to adjust the bed alignment in accordance with an example embodiment. For example, the bed 56 may be adjusted to bring it into correct alignment by machining foot anchors 52 and anchoring them into the floor next to the PET scanner. In an example embodiment, one anchor located near the scanner may serve at a pivot point 54. The other anchors may allow fine adjustment, for example, ~0.04°/screw revolution. In another example embodiment, Teflon or similar low friction surface may be placed under the feet to make sliding easier. Adjustments may be made and then the angle α measurement as described above repeat until the bed is brought into good alignment.

Figure 10:
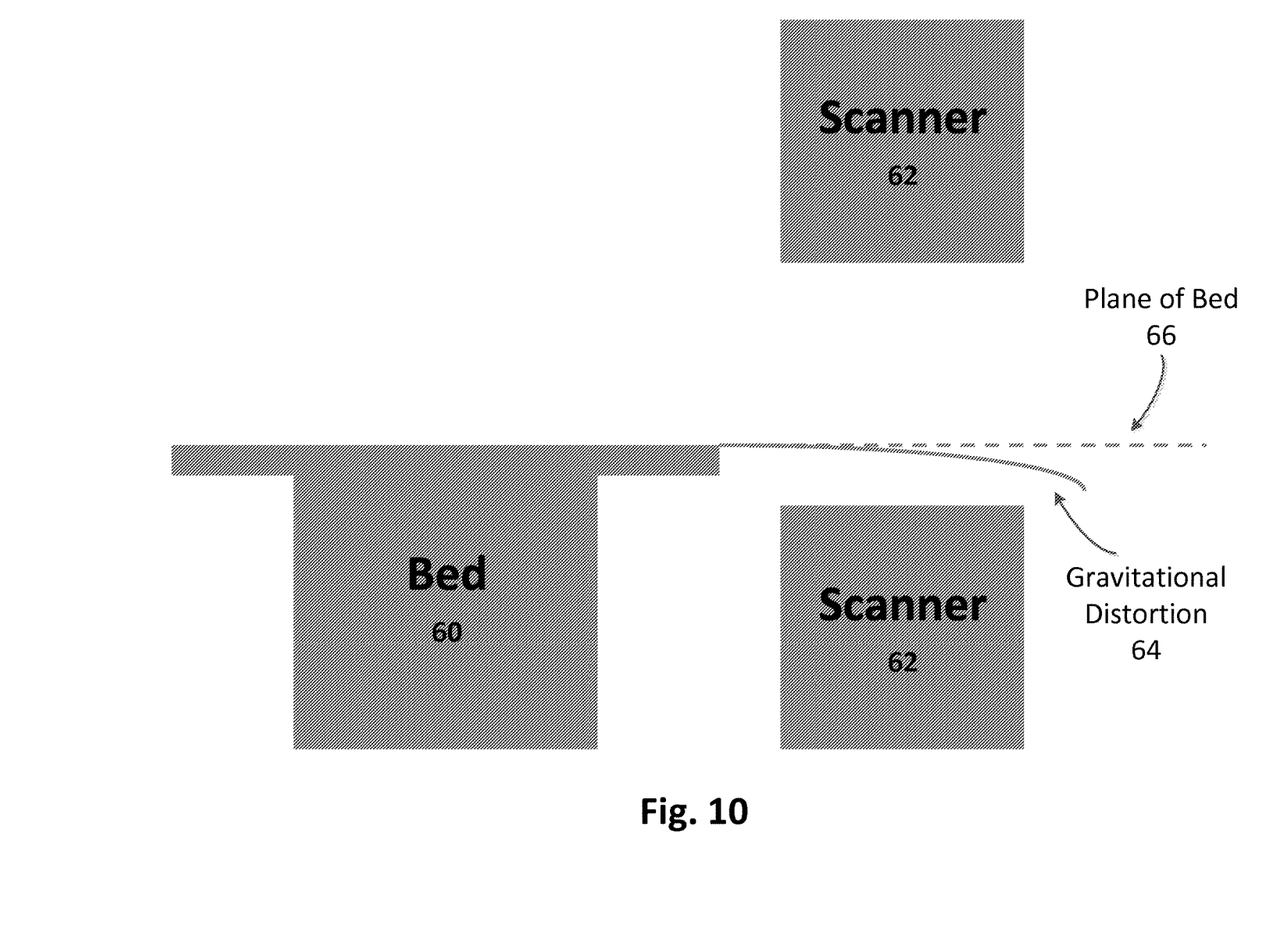
FIG. 10 is a cross section diagram illustrating gravitational deflection of a bed for obtaining super-sampled data in vertical direction in accordance with an example embodiment.

FIG. 10 illustrates gravitational deflection of a bed in accordance with an example embodiment. In this example embodiment, super-sampled data in the vertical direction may be obtained by gravitational deflection while motion of the patient bed results in super-sampled data in the horizontal direction. For example, as a bed 60 moves through the scanner 62, there may be small downward shifts of the bed 60 from the plane of bed 66 due to the gravitational deflection of the bed 60 (i.e. gravitational distortion 64). The size of these shifts may increase progressively as the bed 60 moves further from the bed support and moves through the scanner. This increasing deflection may be used to obtain super-sampled data without additional vertical shifting of the bed 60. This has the advantage of simplifying the acquisition protocol and simultaneously addresses this separate problem that otherwise degrades PET imaging: uncompensated bed deflection. Measurements of the deflection may be performed real-time per patient using either radioactive sources in the bed 60 or a laser positioning system.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. For example, the scanner need not be a 360 degree scanner but the detectors may be distributed around a partial circumference. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. An apparatus for collecting super-sampled imaging data, the apparatus comprising:
    an imaging scanner comprising a plurality of detectors arranged substantially circumferentially about and coaxially along a scanner axis;
    a bed (a) having a planar surface adapted for placement thereon of a target to be scanned, and (b) having a central axis that is generally in the plane of the bed,
    the plurality of detectors defining a plurality of detector lines of response that intersect with one or more reconstructed image volume elements, a volume element defining a volume element distance $V_{D0}$ defined in the direction of the central axis, a volume element distance $V_{D1}$ in the direction of a first axis orthogonal to the central axis, and a volume element distance $V_{D2}$ in the direction of a second axis orthogonal to the central axis and to the first axis; and a first motor, coupled to the bed, for translating the bed along the central axis, wherein the bed is oriented so as to form a first non-zero degree angle between the central axis and the scanner axis and is translated along the central axis by the first motor during scanning by the image scanner, the apparatus being configured to collect, from at least one of the plurality of detectors, super-sampled imaging data of the target to be scanned, the super-sampled data comprising (a) data collected from the target when the target is located at a first spatial location and (b) data collected from the target when the target has been (i) displaced from the first spatial location along the direction of the scanner axis by a non-integer multiple of volume element distance $V_{D0}$, (ii) displaced from the first spatial location along the direction of the first axis by a non-integer multiple of the volume element distance $V_{D1}$, (iii) displaced from the first spatial location along the direction of the second axis by a non-integer multiple of volume element distance $V_{D2}$, or any combination of (i), (ii), and (iii);

the apparatus being configured to effect image reconstruction using the super-sampled imaging data.

2. The apparatus of claim 1, further comprising a second motor for translating the bed along an axis orthogonal to both the central axis and the scanner axis for acquiring super-sampled data in an additional dimension.

3. The apparatus of claim 1, further comprising one or more actuators that change the orientation of the bed, thereby changing the first non-zero degree angle.

4. The apparatus of claim 1, wherein the bed is oriented so as to form a second non-zero degree angle between the central axis and an axis orthogonal to the scanner axis.

5. The apparatus of claim 4, wherein the axis orthogonal to the scanner axis is a horizontal axis.

6. The apparatus of claim 4, wherein the axis orthogonal to the scanner axis is a vertical axis.

7. The apparatus of claim 4, further comprising one or more actuators that change the orientation of the bed, thereby changing the second non-zero degree angle.

8. The apparatus of claim 4, wherein the second non-zero degree angle is an angle that maximizes sampling uniformity, wherein sampling uniformity is the normalized standard deviation of the weighted distances of super-sampling points in a unit cell to all points in that unit cell.

9. The apparatus of claim 1, wherein the first non-zero degree angle is an angle that maximizes sampling uniformity, wherein sampling uniformity is the normalized standard deviation of the weighted distances of super-sampling points in a unit cell to all points in that unit cell.

10. The apparatus of claim 1, wherein the plurality of detectors are capable of detecting gamma rays, x-rays, or any combination thereof.

11. The apparatus of claim 1, wherein the bed is configured to allow at least one portion of the bed to shift progressively downward from the plane of the bed as the bed moves through the scanner.

12. A method for collecting super-sampled imaging data, the method comprising:
positioning a subject that has been treated with a radioactive tracer capable of causing the emission of detectable particles on a bed having a planar surface on which the subject is placed and having a central axis that is generally in the plane of the bed;
orienting the bed so as to form a first non-zero degree angle between the central axis and a scanner axis of a scanner;
translating the bed along the central axis;
detecting the emission of the detectable particles with a plurality of detectors arranged substantially circumferentially about the scanner axis of the scanner,
the plurality of detectors defining a plurality of detector lines of response that intersect with one or more reconstructed image volume elements, a volume element defining a volume element distance $V_{D0}$ defined in the direction of the central axis, a volume element distance $V_{D1}$ in the direction of a first axis orthogonal to the central axis, and a volume element distance $V_{D2}$ in the direction of a second axis orthogonal to the central axis and to the first axis
the detecting being performed so as to collect super-sampled imaging data of the subject,
the super-sampled data comprising (a) data collected from the target when the target is located at a first spatial location and (b) data collected from the target when the target has been (i) displaced from the first spatial location along the direction of the scanner axis by a non-integer multiple of volume element distance $V_{D0}$, (ii) displaced from the first spatial location along the direction of the first axis by a non-integer multiple of the volume element distance $V_{D1}$, (iii) displaced from the first spatial location along the direction of the second axis by a non-integer multiple of volume element distance $V_{D2}$, or any combination of (i), (ii), and (iii).

13. The method of claim 12, further comprising:
transmitting radiation from the scanner toward the target; and
repeating the steps of transmitting radiation from the scanner toward the target, translating the bed along the central axis, and detecting the emission of the detectable particles with the scanner.

14. The method of claim 12, further comprising repeating the steps of translating the bed along the central axis and detecting the emission of the detectable particles with the scanner.

15. The method of claim 12, further comprising:
translating the bed along an axis that is substantially orthogonal to the central axis.

16. The method of claim 12, wherein the bed is oriented so as to form a second non-zero degree angle between the central axis and an axis orthogonal to the scanner axis.

17. The method of claim 16, wherein the axis orthogonal to the scanner axis is a horizontal axis.

18. The method of claim 16, wherein the axis orthogonal to the scanner axis is a vertical axis.

19. The method of claim 16, further comprising translating the bed to form the second non-zero degree angle between the central axis and an axis orthogonal to the scanner axis.

20. The method of claim 12, wherein said positioning step includes at least one portion of the bed shifting progressively downward from the plane of the bed as the bed moves through the scanner.

21. The method of claim 13, further comprising reconstructing an image of the target from the collected super-sampled imaging data of the target.

* * * * *